United States Patent
Kim et al.

(10) Patent No.: US 10,160,622 B2
(45) Date of Patent: Dec. 25, 2018

(54) SELF-POWERED HANDRAIL STERILIZING DEVICE AND INFORMATION COLLECTING DEVICE USING HANDRAIL STERILIZING DEVICE

(71) Applicant: SOOKYOUNG A.I.D CO., LTD., Yangcheon-gu, Seoul (KR)

(72) Inventors: Kyoung-Youn Kim, Seoul (KR); Chi-Young Kang, Incheon (KR); Hyun-Seog Kim, Suwon-si (KR)

(73) Assignee: SOOKYOUNG A.I.D. CO., LTD., Yangcheon-gu, Seoul (KR)

( * ) Notice: Subject to any disclaimer, the term of this patent is extended or adjusted under 35 U.S.C. 154(b) by 0 days.

(21) Appl. No.: 15/559,261

(22) PCT Filed: Jan. 28, 2016

(86) PCT No.: PCT/KR2016/000954
§ 371 (c)(1),
(2) Date: Sep. 18, 2017

(87) PCT Pub. No.: WO2016/148389
PCT Pub. Date: Sep. 22, 2016

(65) Prior Publication Data
US 2018/0099842 A1      Apr. 12, 2018

(30) Foreign Application Priority Data

Mar. 19, 2015  (KR) ........................ 10-2015-0038133
Jun. 16, 2015  (KR) ........................ 10-2015-0085235

(51) Int. Cl.
*B65G 45/18*   (2006.01)
*B66B 23/04*   (2006.01)
(Continued)

(52) U.S. Cl.
CPC ................ *B66B 23/04* (2013.01); *A61L 2/08* (2013.01); *A61L 2/18* (2013.01); *A61L 2/26* (2013.01);
(Continued)

(58) Field of Classification Search
CPC .......... B66B 31/00; B66B 30/02; B65G 45/18
(Continued)

(56) References Cited

U.S. PATENT DOCUMENTS 4,934,512 A      6/1990  Lin et al.
7,854,313 B1 *  12/2010  Gotsche .................. B66B 31/02
                                                              198/495
(Continued)

FOREIGN PATENT DOCUMENTS

KR    1019990027216       4/1999
KR    1020090045452 A     5/2009
(Continued)

OTHER PUBLICATIONS

International Search Report Corresponding to PCT/KR2016/000954 dated Jun. 7, 2016.
(Continued)

*Primary Examiner* — James R Bidwell
(74) *Attorney, Agent, or Firm* — Davis & Bujold PLLC; Michael J. Bujold

(57) ABSTRACT

Disclosed herein are a self-powered type handrail sterilizing device and a device for collecting visitor information using the same. The self-powered type handrail sterilizing device includes: a housing having an opening fastened to a handrail of an escalator or a moving walk; a power unit installed at an inner side of the housing to convert a rotational motion depending on driving of the handrail into power; and a ultraviolet lamp module installed on an inner surface of the
(Continued)

opening of the housing and configured to irradiate sterilizing light to the handrail through the power of the power unit.

13 Claims, 12 Drawing Sheets

(51) Int. Cl.
    *A61L 2/08*     (2006.01)
    *B66B 23/24*     (2006.01)
    *B66B 31/02*     (2006.01)
    *A61L 2/18*     (2006.01)
    *A61L 2/26*     (2006.01)
    *B65G 45/22*     (2006.01)

(52) U.S. Cl.
    CPC .............. *B66B 23/24* (2013.01); *B66B 31/02* (2013.01); *B65G 45/22* (2013.01)

(58) Field of Classification Search
    USPC ................ 198/321, 326, 335, 337, 494, 496
    See application file for complete search history.

(56) References Cited

U.S. PATENT DOCUMENTS

| | | | |
|---|---|---|---|
| 9,415,129 B2 | 8/2016 | Yukimoto | |
| 2012/0273003 A1* | 11/2012 | Holloway | A61L 2/16 15/256.5 |
| 2014/0322073 A1* | 10/2014 | Link | A61L 2/10 422/24 |
| 2017/0217735 A1* | 8/2017 | Ibrahim | B66B 31/02 |

FOREIGN PATENT DOCUMENTS

| | | | | |
|---|---|---|---|---|
| KR | 10-2014-0086835 A | | 7/2014 | |
| KR | 10-1413217 B1 | | 7/2014 | |
| KR | 10-2014-0145214 A | | 12/2014 | |
| WO | 2010/021506 | * | 2/2010 | ............ B66B 23/24 |
| WO | 2013/018054 A2 | | 2/2013 | |

OTHER PUBLICATIONS

Written Opinion Corresponding to PCT/KR2016/000954 dated Jun. 7, 2016.

* cited by examiner

SELF-POWERED HANDRAIL STERILIZING DEVICE AND INFORMATION COLLECTING DEVICE USING HANDRAIL STERILIZING DEVICE

TECHNICAL FIELD

The present invention relates to a self-powered type handrail sterilizing device capable of being simply installed at an existing escalator or moving walk, and a device for collecting visitor information using the same.

BACKGROUND ART

Generally, an escalator or a moving walk is configured to continuously move around a fixed frame corresponding to an axis, and is used in places in which there are many people, for example, subways, department stores, airports, and the like.

Such an escalator or a moving walk is installed with a handrail moving together with movement of a moving plate, and pedestrians get an education to hold the handrail in consideration of an emergency situation such as reverse traveling, a sudden stop, or the like.

Therefore, many bacteria are inhabited in the handrail, which is a main factor in inflecting an infectious disease such as a cold or pneumonia.

As technology of cleaning the handrail of the escalator, for example, U.S. Pat. No. 4,934,512 (entitled "CLEANING DEVICE FOR ARMREST BELT CONVEYOR OF THE ELECTRIC ESCALATOR") in which the handrail is moistened with water, the handrail is cleaned, and the water is removed by a cleaning tool has been suggested.

However, this device should include a water tank in which a detergent is contained, such that a volume of the device is increased and a structure of the device is complicated.

In addition, in the case in which the handrail is moistened with a large amount of water when it is moistened with the water, the water permeates into a space between the handrail and the fixed frame, such that there is a risk that a chain driving the handrail will be corroded.

Meanwhile, Korean Patent Laid-Open Publication No. 10-1999-027216 (entitled "DEVICE FOR CLEANING SURFACE OF HANDRAIL FOR MOVING WAY") has also been suggested. This device configured to clean a surface of a handrail using a brush may remove dust, but has a difficulty in cleaning a stain, or the like, having viscosity. In addition, it is impossible to prevent propagation of bacteria, or the like, through the surface of the handrail.

DISCLOSURE

Technical Problem

An object of the present invention is to provide a handrail sterilizing device capable of being simply installed at an existing escalator or moving walk, and a device for collecting visitor information using the same.

Technical Solution

According to an exemplary embodiment of the present invention, a self-powered type handrail sterilizing device may include: a housing having an opening fastened to a handrail of an escalator or a moving walk; a power unit installed at an inner side of the housing to convert a rotational motion depending on driving of the handrail into power; and a ultraviolet lamp module installed on an inner surface of the opening of the housing and configured to irradiate sterilizing light to the handrail through the power of the power unit.

The power unit may include: a roller unit movably closely adhered to a main surface of the handrail and rotated; a gear unit configured to interlock with the roller unit; and a power generating unit configured to generate the power by interlocking with the gear unit.

The power unit may further include a pressing unit configured to press the roller unit.

The ultraviolet lamp module may include: a board attached to an inner peripheral surface of the opening of the housing; an ultraviolet lamp attached to one surface of the board to irradiate the sterilizing light toward the handrail; and a cleaning brush fixed to an inner peripheral surface of the housing to remove foreign materials of the handrail.

The ultraviolet lamp may include a first sub-lamp and a second sub-lamp installed with the cleaning brush interposed therebetween.

The ultraviolet lamp may be installed to irradiate the sterilizing light in a direction parallel with a moving direction of the handrail, and the ultraviolet lamp module may further include a lampshade-like reflector configured to reflect the sterilizing light toward the handrail.

The self-powered type handrail sterilizing device may further include a protecting cover surrounding an outer portion of the housing.

The self-powered type handrail sterilizing device may further include an indicator lamp installed on the other surface of the board to emit light through the power of the power unit, wherein the protecting cover further includes a light transparent portion formed at a position corresponding to that of the indicator lamp.

According to another exemplary embodiment of the present invention, a device for collecting visitor information using a handrail sterilizing device may include: the self-powered type handrail sterilizing devices as described above installed at both sides of a handrail of an escalator to face each other, wherein at least one of the self-powered type handrail sterilizing devices includes: a detecting sensor configured to sense a person passing through the escalator; a communication module configured to transmit and receive data to and from an external device; and a controller configured to transmit information on a visitor transmitted from the detecting sensor through the communication module.

According to still another exemplary embodiment of the present invention, a self-powered type handrail sterilizing device may include: a frame having a handrail fastening groove formed therein; a cover case covering the frame and having an opening into which the handrail is fitted; a self power source unit installed at an inner side of the frame and pressedly closely adhered to the handrail to convert a rotational motion depending on driving of the handrail into power source; a power source board installed at any one of an outer side of the frame and an inner side of the cover case to rectify and stabilize the power source of the self power source unit; and a ultraviolet lamp module installed at the inner side of the frame to receive the power source from the power source board and irradiate sterilizing light to the handrail.

The cover case may include: a front cover corresponding to a front of the frame and having both side surfaces rounded in order to protect a pedestrian; and a pair of side covers installed at both sides of the front cover.

A lower surface of the front cover may be rounded in order to prevent an external object from being inserted into the handrail.

The side cover may include: a side cover base in which a circular recess and a fastening hole formed in the center of the circular recess are formed; and a screw fastening portion screw-coupled to the fastening hole to fasten the side cover base and the frame to each other and having a head portion having a size corresponding to a size of the circular recess.

The self-powered type handrail sterilizing device may further include a sliding door portion installed in an opening of each of the side covers to adjust a size of the opening depending on a size of the handrail.

The self power source unit may include: a power source case divided into a first region and a second region; a support rod for supporting the power source case; a roller unit installed in the first region and closely adhered to a main surface of the handrail to be thus rotated depending on driving of the handrail; a power generating unit installed in the second region and configured to generate the power source by interlocking with the roller unit; and a spring fitted onto the support rod to pressedly closely adhere the power source case to the handrail.

The power source case may include: a first power source side case; a second power source side case having a mirror shape with respect to the first power source side case; and a power source fastening portion fastening the first power source side case and the second power source side case to each other.

A heat radiation hole may be formed in the power source case in order to radiate heat of the power generating unit.

The ultraviolet lamp module may include: a reflecting plate attached to an inner side of a front of the frame; a board installed on the reflecting plate; ultraviolet lamps attached to one surface of the board to irradiate the sterilizing light toward the handrail, and installed in pair; and a handrail brush installed between the ultraviolet lamps, and the handrail brush being detachably attached to the frame, and wherein a brush rail extended from the brush groove may be formed in the frame, and the handrail brush may include a fixed portion fitted into the brush rail, and a brush portion attached to an upper surface of the fixed portion.

Advantageous Effects

According to an exemplary embodiment of the present invention having the configuration described above, the self-powered type handrail sterilizing device may be mounted at the existing escalator or moving walk in a simple structure, and may sterilize harmful bacteria inhabited in the handrail to contribute to public health.

In addition, an irradiation range of the sterilizing light is increased, thereby making it possible to maximize a sterilizing effect.

In addition, information on persons visiting through the escalator, or the like, is collected, thereby making it possible to provide basic information on calculation of an advertisement cost for an advertisement, or the like, installed in the vicinity of the escalator.

BEST MODE

Figure 1:
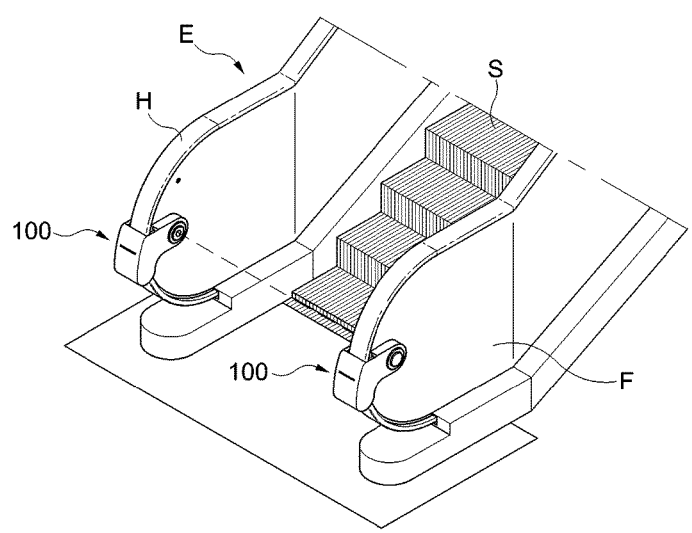
FIG. 1 is a view illustrating an example in which self-powered type handrail sterilizing devices according to first and third exemplary embodiments of the present invention are applied to an escalator.

Hereinafter, a self-powered type handrail sterilizing device and a device for collecting visitor information using the same according to exemplary embodiments of the present invention will be described in detail with reference to the accompanying drawings. Throughout the present disclosure, components that are the same as or similar to each other will be denoted by reference numerals that are the same as or similar to each other and a description therefor will be replaced by the first description, in different exemplary embodiments.

FIG. 1 is a view illustrating an example in which self-powered type handrail sterilizing devices according to first and third exemplary embodiments of the present invention are applied to an escalator. As illustrated in FIG. 1, an escalator E may include a transfer stair portion S transferring visiting persons and handrails H installed at both sides of the transfer stair portion S. The handrail sterilizing devices 100 according to the present invention may be installed at lower sides of the handrails H adjacent to an entrance and an exist, and may be installed at two handrails H to face each other as illustrated in FIG. 1.

The handrail sterilizing device 100 according to the present invention converts kinetic energy by which the handrail is moved into electrical energy to drive an ultraviolet lamp module 30 installed in the handrail sterilizing device 100, thereby sterilizing various kinds of bacteria inhabited in the handrail, and removes foreign materials such as dust, or the like, by a cleaning brush 35 to allow the handrail to be always maintained in a clean state.

Hereinafter, a detailed configuration of the handrail sterilizing device 100 installed at the handrail as illustrated in FIG. 1 will be described in more detail with reference to FIGS. 2 to 5.

Figure 2:
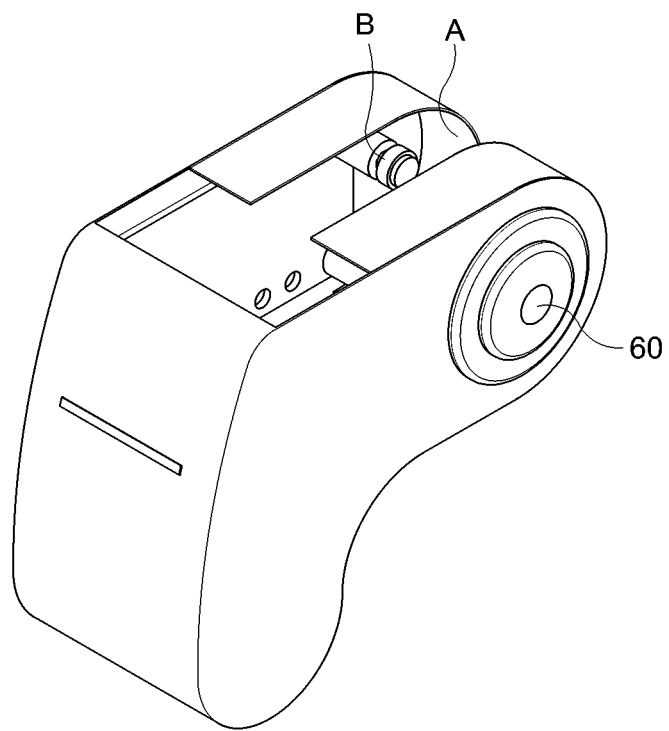
FIG. 2 is a perspective view illustrating a self-powered type handrail sterilizing device according to a first exemplary embodiment of the present invention.
Figure 3:
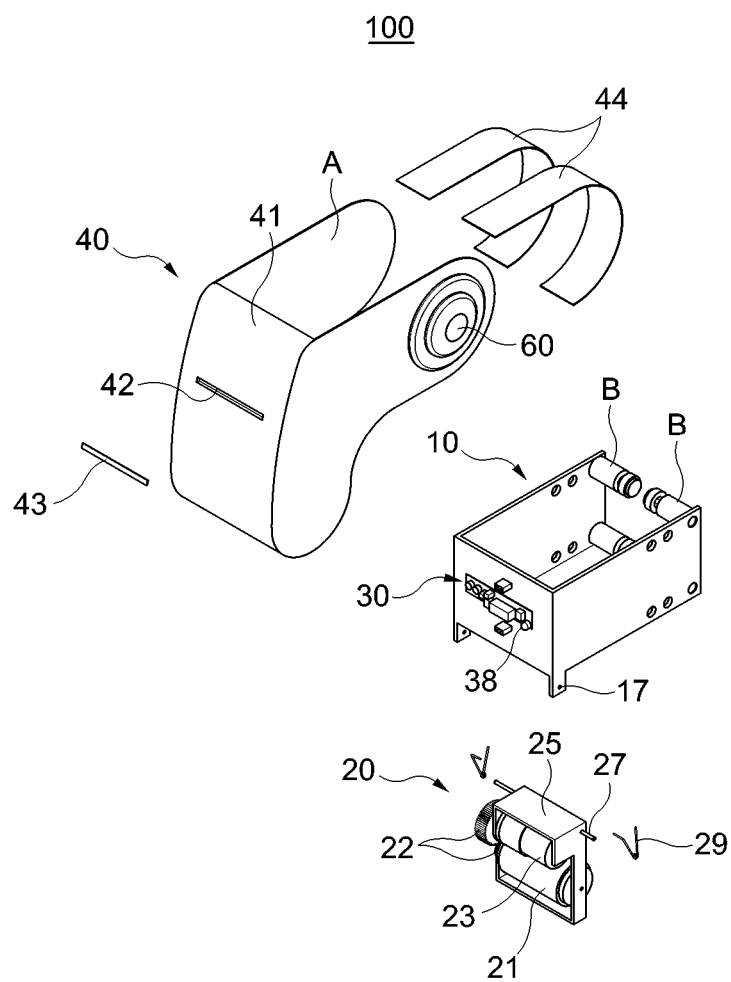
FIG. 3 is an exploded perspective view illustrating the self-powered type handrail sterilizing device according to a first exemplary embodiment of the present invention.
Figure 4:
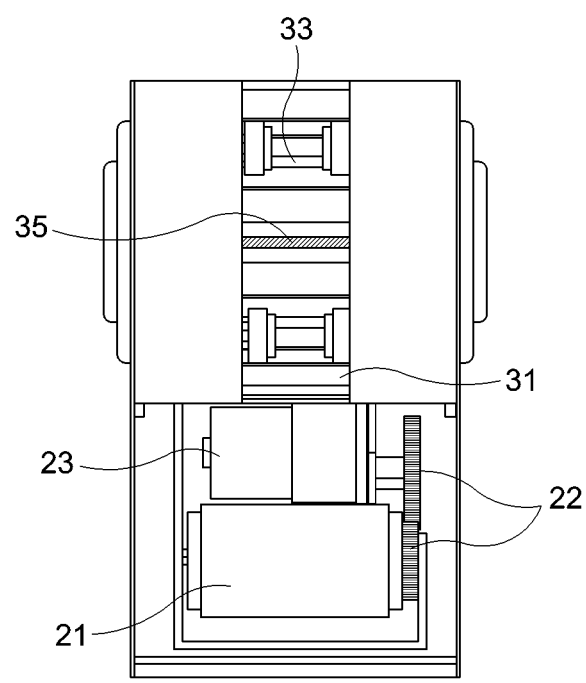
FIG. 4 is a rear view illustrating the self-powered type handrail sterilizing device according to a first exemplary embodiment of the present invention.
Figure 5:
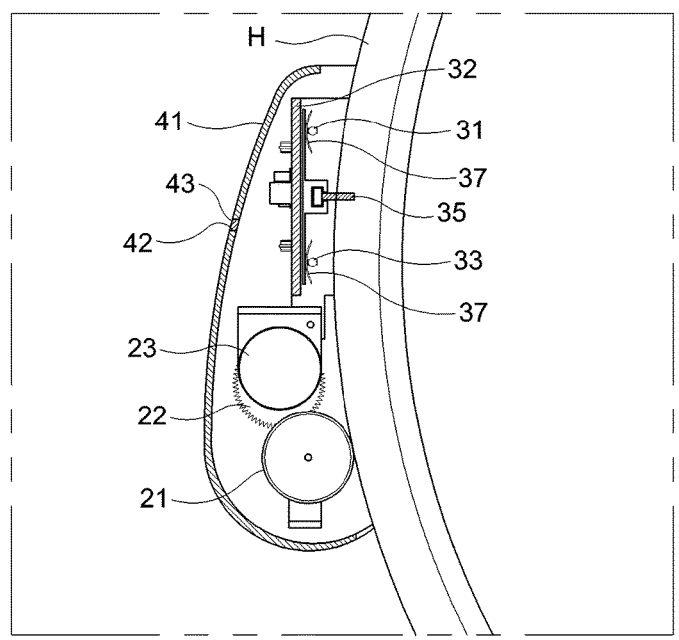
FIG. 5 is a cross-sectional view illustrating the self-powered type handrail sterilizing device according to a first exemplary embodiment of the present invention.

FIG. 2 is a perspective view illustrating a self-powered type handrail sterilizing device according to a first exemplary embodiment of the present invention, FIG. 3 is an exploded perspective view illustrating the self-powered type handrail sterilizing device according to a first exemplary embodiment of the present invention, FIG. 4 is a rear view illustrating the self-powered type handrail sterilizing device according to a first exemplary embodiment of the present invention, and FIG. 5 is a cross-sectional view illustrating the self-powered type handrail sterilizing device 100 according to an exemplary embodiment of the present invention.

As illustrated in FIG. 2, the handrail sterilizing device 100 according to the present invention generally has a '⌐' shape, and has an insertion portion A formed at one side thereof so that it may be fitted onto the handrail, and the insertion portion A is installed with fixing members B for fixing the handrail sterilizing device to a frame F (formed of a tempered glass, a metal, or a plastic) (see FIG. 1) of the escalator or a moving walk. Here, the fixing members B are fastened to the frame through compression to fix the handrail sterilizing device 100.

Referring to FIGS. 3 to 5, the handrail sterilizing device 100 according to a first exemplary embodiment of the present invention may be configured to mainly include a housing 10, a power unit 20, an ultraviolet lamp module 30, and a cover 40.

The housing 10 may have an opening fastened to the handrail of the escalator or the moving walk, have the ultraviolet lamp module 30 installed on an inner surface thereof, and may have fastened holes 17 into which the power unit 20 is to be fastened.

The power unit 20 is installed at an inner side of the housing 10 to serve to convert a rotational motion depending on driving of the handrail into power. In more detail, the power unit 20 may include a roller unit 21 movably closely adhered to a main surface moved in the handrail and rotated depending on movement of the handrail, gear units 22 interlocking with the roller unit 21 depending on the rotation of the roller unit 21, and a power generating unit 23 generating power by interlocking with the gear units 22 and transferring the power to the ultraviolet lamp module 30. The power generating unit 23 is coupled to a casing 25 as illustrated, and a fastened pin 27 is formed at one end of the casing 25. The fastened pin 27 is fastened into the fastened hole 17 of the housing 10.

Meanwhile, when the fastened pin 27 is fastened into the fastened hole 17, the fastened pin 27 is fastened into the fastened hole 17 through a pressing spring (a pressing unit) 29. The pressing spring 29 presses the casing 25 to the handrail to allow the roller unit 21 to be closely adhered to the handrail. Therefore, even in the case in which the handrail is moved in a curved form, the roller unit 21 may be stably closely adhered to the handrail.

Referring to FIGS. 3 and 4, the ultraviolet lamp module 30 may be configured to include a board 32 having electronic components E such as a rectifier rectifying power source supplied from the power unit 20, an alternating current (AC) to direct current (DC) converter changing the power into DC power source, and the like, mounted thereon at a side opposite to the handrail and attached to an inner surface of the opening of the housing 10, ultraviolet lamps 31 and 33 installed in a handrail direction on the other surface of the board 32 to irradiate sterilizing light toward the handrail, lampshade-like reflectors 37 reflecting the sterilizing light of the ultraviolet lamps 31 and 33, and a cleaning brush 35 installed adjacently to the ultraviolet lamps 31 and 33 to remove foreign materials of the handrail.

The structure of the ultraviolet sterilizing lamp described above will be described in more detail with reference to FIGS. 6 and 7.

The cover 40 is a component for preventing the power unit 20 and the ultraviolet lamp module 30 from being exposed to the outside and protecting the power unit 20 and the ultraviolet lamp module 30 from external impact.

In more detail, the cover 40 may include a cover body 41, a light transparent hole formed in the cover body 41, and cover members 44.

A light transparent hole 42 is formed at a central portion of the cover body 41, and is covered with a translucent member 43. Therefore, light of an indicator lamp 38 attached to the board 32 is viewed from the outside, and it may be confirmed from the outside whether or not the handrail sterilizing device 100 is operated.

A structure of an ultraviolet lamp module 30 of the self-powered type handrail sterilizing device according to a first exemplary embodiment of the present invention will hereinafter be described in more detail with reference to FIGS. 6 and 7.

Figure 6:
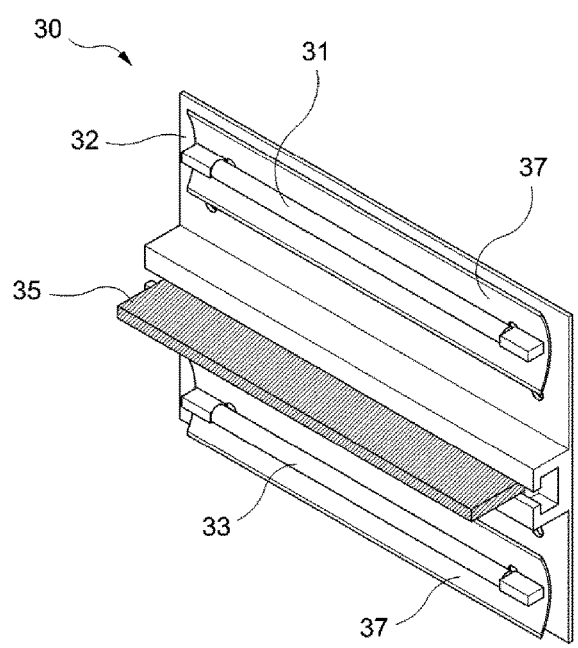
FIG. 6 is a front perspective view illustrating an ultraviolet lamp module of the self-powered type handrail sterilizing device according to a first exemplary embodiment of the present invention.
Figure 7:
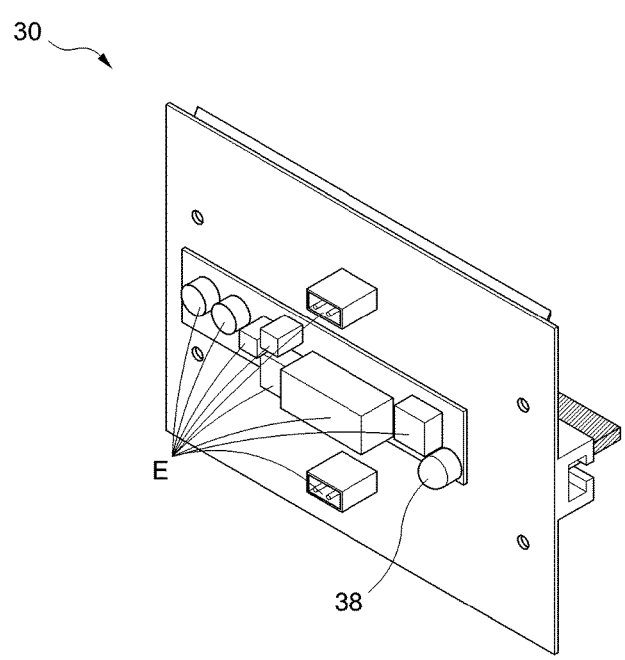
FIG. 7 is a rear perspective view illustrating the ultraviolet lamp module of the self-powered type handrail sterilizing device according to a first exemplary embodiment of the present invention.

FIG. 6 is a front perspective view illustrating an ultraviolet lamp module of the self-powered type handrail sterilizing device according to a first exemplary embodiment of the present invention, and FIG. 7 is a rear perspective view illustrating the ultraviolet lamp module of the self-powered type handrail sterilizing device according to a first exemplary embodiment of the present invention. As illustrated in FIG. 6, in the ultraviolet lamp module 30, the electronic components E are mounted on one surface of the board 32, and the indicator lamp 38 for confirming operations of the ultraviolet lamps 31 and 33 is also mounted on one surface of the board 32. Light of the indicator lamp 38 is irradiated to the light transparent hole 42 of the cover 40, and it may thus be confirmed from the outside whether or not the handrail sterilizing device 100 according to the present invention is operated.

As illustrated in FIG. 7, in the ultraviolet lamp module, the cleaning brush 35 is fixed and installed between two lamps, that is, a first sub-lamp 31 and a second sub-lamp 33, and serves to remove foreign materials of the moving handrail.

Meanwhile, the first sub-lamp 31 and the second sub-lamp 33 are installed to irradiate sterilizing light in a direction parallel with a moving direction of the handrail, and the sterilizing light is reflected by the lampshade-like reflectors 37 having an arc shape to be irradiated toward the handrail. Through the configuration as described above, an irradiation range of the sterilizing light may be maximally increased, such that a sterilizing effect may be improved. That is, an irradiation time of the sterilizing light is more important than intensity of the sterilizing light in the sterilizing effect, and according to the configuration of the present invention, the irradiation range of the sterilizing light is increased, such that the sterilizing light may be irradiated to the handrail, which is a sterilizing target, for a longer period of time. Therefore, the sterilizing effect may be maximized.

Therefore, some of the sterilizing light of the first sub-lamp 31 and the second sub-lamp 33 may be directed toward the cleaning brush 35 to prevent bacteria from being inhabited in the cleaning brush 35.

Electronic components of a device 200 for collecting visitor information using a self-powered type handrail sterilizing device 100 according to another exemplary embodiment of the present invention will hereinafter be described with reference to FIG. 8.

Figure 8:
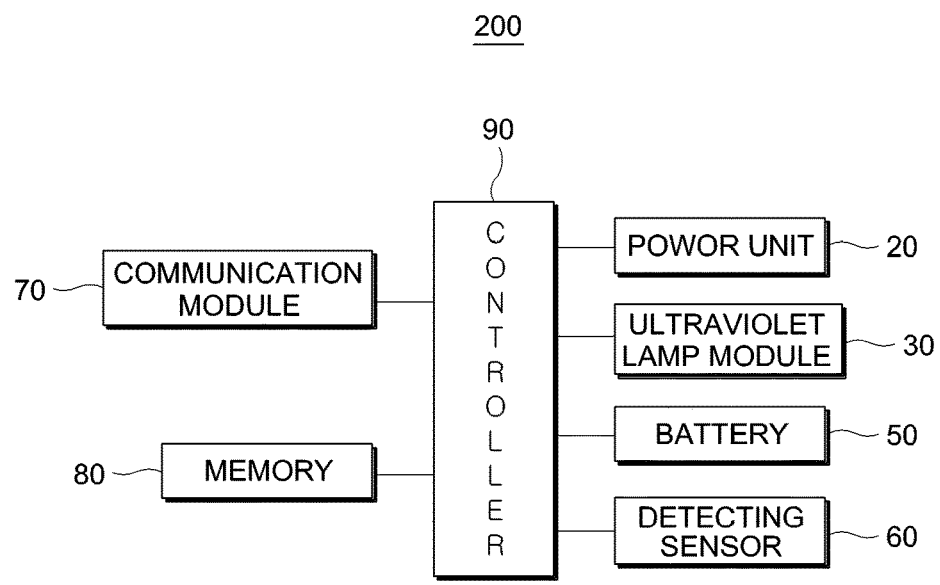
FIG. 8 is a block diagram for describing electronic components of a device for collecting visitor information using a self-powered type handrail sterilizing device according to another exemplary embodiment of the present invention.

FIG. 8 is a block diagram for describing electronic components of a device 200 for collecting visitor information using a self-powered type handrail sterilizing device according to another exemplary embodiment of the present invention. The device 200 for collecting visitor information using a self-powered type handrail sterilizing device 100 according to an exemplary embodiment of the present invention may be configured to include a power unit 20, an ultraviolet lamp module 30, a battery 50, a detecting sensor 60, a communication module 70, a memory 80, and a controller 90.

Here, the power unit 20 and the ultraviolet lamp module 30 have been already described, and a detailed description therefor will thus be omitted.

The battery 50 is charged with the power generated from the power unit 20 to serve to supply the power to the ultraviolet lamp module 30, the detecting sensor 60, the communication module 70, the controller 90, and the like. The battery 50, which is a secondary battery, is a component charged by the power unit 20 and discharged depending on power consumption of the ultraviolet lamp module 30, and the like.

The detecting sensor 60 is a component installed on a side surface of the housing 10 to detect a person moved by the escalator or the moving walk, thereby generating personal information. As the detecting sensor 60, a photo-coupler including a light receiving unit and a light emitting unit each installed in facing handrail sterilizing devices 100 may be used or various kinds of human body detecting sensors, for example, an ultrasonic sensor, and the like, may be used.

In addition, in the case in which a camera is used as the detecting sensor 60, the personal information may distinguish whether a person is male or female, whether a person is a child or an adult, or the like. Therefore, more detailed personal information may be created.

The communication module 70 serves to transmit visitor information, that is, the personal information, obtained by the detecting sensor 60 to an external device depending on a control of the controller 90. Here, the external device is a server of a company managing a bill board positioned in the vicinity of the escalator or the moving walk, such as a subway advertisement managing server, or the like.

The memory 80 serves to store the personal information and a driving program of the device 200 for collecting visitor information according to the present invention. The controller 90 operates the driving program to drive sterilizing lamps and transmit the visitor information from the detecting sensor 60 to the communication module 70.

A self-powered type handrail sterilizing device according to a second exemplary embodiment of the present invention will hereinafter be described in more detail with reference to FIGS. 9 to 14.

Figure 9:
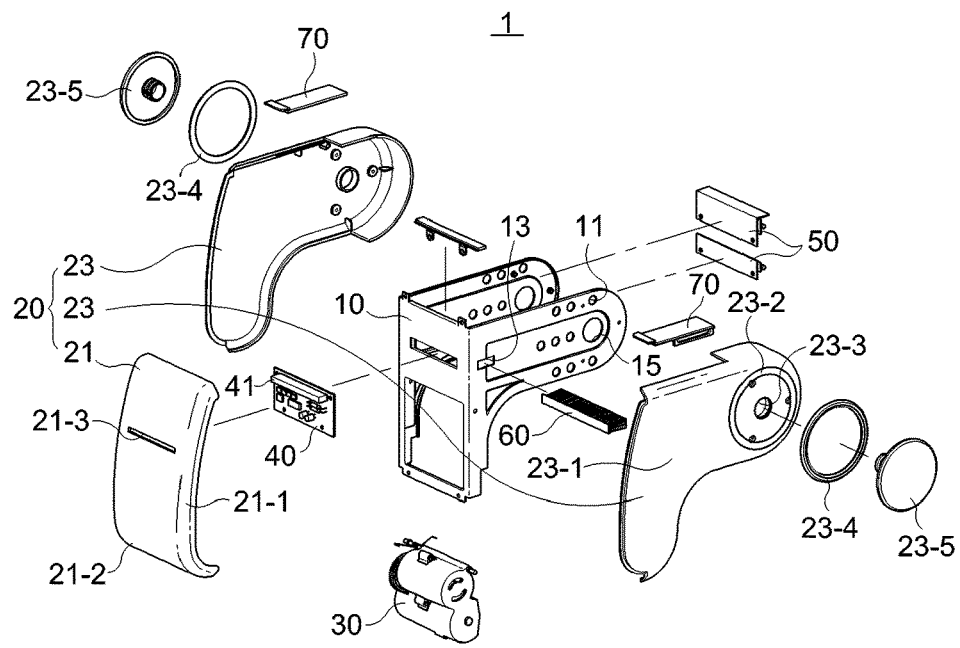
FIG. 9 is an exploded perspective view illustrating a self-powered type handrail sterilizing device according to a second exemplary embodiment of the present invention.

FIG. 9 is an exploded perspective view illustrating a self-powered type handrail sterilizing device according to a second exemplary embodiment of the present invention. As illustrated in FIG. 9, a self-powered type handrail sterilizing device 100' according to an exemplary embodiment of the present invention may be configured to include a frame 10', a self power source unit 30', a power source board 40', ultraviolet lamp modules 50', a brush 60', and a sliding door portion 70'.

The frame 10' is a component having handrail fastening grooves 11' formed in side surfaces thereof, and fixing units (for example, bolt fastening portions) that are to be fastened to a handrail plate P' may be inserted into the handrail fastening grooves 11'. The frame 10' is a component constituting a framework of the self-powered type handrail sterilizing device. The frame 10' may be formed of a metal such as SUS for the purpose of durability. As illustrated in FIG. 9, the handrail fastening grooves 11', brush fastening grooves 13', and cover fastening grooves 15' are formed in the frame 10' and the ultraviolet lamp modules 50' irradiating sterilizing light are attached to an inner side of the frame 10'.

A cover case 20' is a component forming an appearance of the self-powered type handrail sterilizing device 100' according to an exemplary embodiment of the present invention and protecting the frame 10' from the outside. In more detail, the cover case 20' includes a front cover 21' and side covers 23', and the power source board 40' rectifying and stabilizing power of the self power source unit 30' is separably installed at an inner side of the front cover 21'. In addition, the side covers 23' is configured to be fastened to the frame 10' through a screw coupling portion 23'-5. Therefore, in the case in which a fault occurs in the power source board 40', the screw coupling portion 23'-5 is separated from the frame 10', such that separation of the front cover 21' is possible, and replacement of the power source board 40' is thus possible. A structure of the cover case 20' will be described in more detail with reference to FIG. 10.

The power source board 40' is attached to the cover case 20' in the present detailed description, but it is to be understood that the power source board 40' may be attached to the frame 10'.

The self power source unit 30' is a component installed at an inner side of the frame 10' and pressedly and closely adhered to the handrail to convert a rotational motion depending on driving of the handrail into power source. In the present invention, the self power source unit 30' has a power generating unit and a roller unit embedded in a power source case. This will be described in more detail with reference to FIG. 12.

The power source board 40' is separably installed at the inner side of the front cover 21' by screw coupling to serve to rectify and stabilize unstable power supplied from a self power generating unit and supply the power source to the ultraviolet lamp modules 50' installed at the inner side of the frame 10'. Meanwhile, an indicator light emitting unit 41' is disposed on the power source board to irradiate operation light to a light transparent portion 21'-3 of the front cover 21'.

The ultraviolet lamp modules 50' are installed at the inner side of the frame 10' to serve to receive the power source from the power source board 40' and irradiate sterilizing light to the handrail to sterilize bacteria or viruses inhabited in the handrail. In the present invention, a pair of ultraviolet lamp modules 50' are installed in order to create a sufficient irradiated light region, and a handrail brush 60' is installed between pair of ultraviolet lamp modules 50' in order to remove foreign materials such as fine dust, or the like. Structures of the ultraviolet lamp modules 50' and the handrail brush 60' will be described in more detail with reference to FIG. 13.

The sliding door portion 70' is a component attached to the side covers 23' and extended or contracted depending on a thickness of the handrail H. Since it is possible to prevent foreign materials from entering between the side covers 23' and the handrail H by the sliding door portion 70', it is possible to prevent dust from becoming a cause of a fault. Installation and an operation of the sliding door portion 70' will be described in more detail with reference to FIG. 4.

Hereinafter, structures of the cover case 20' the self power source unit 30', the handrail brush 60, the ultraviolet lamp modules 50', the handrail brush 60', and the sliding door portion 70' will be described in more detail with reference to FIGS. 10 to 14.

Figure 10:
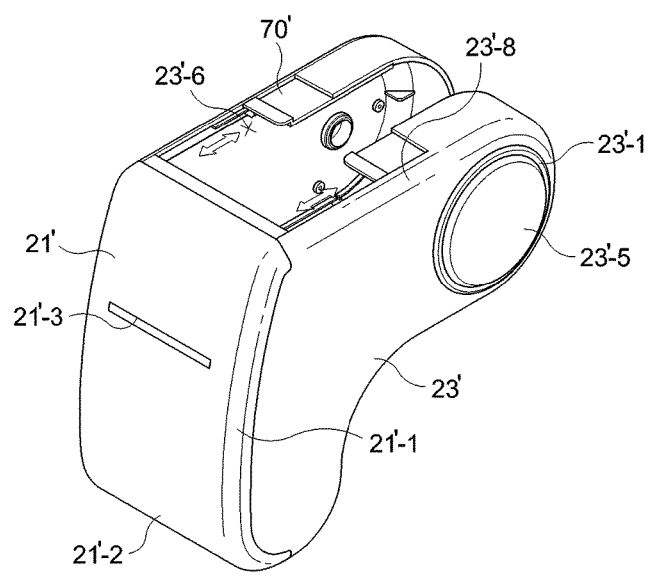
FIG. 10 is a perspective view illustrating a cover case of the self-powered type handrail sterilizing device according to a second exemplary embodiment of the present invention.

FIG. 10 is a perspective view illustrating a cover case of the self-powered type handrail sterilizing device according to a second exemplary embodiment of the present invention. As illustrated in FIG. 10, edge portions of the front cover 21' and the side cover 23' are rounded (a side round portion 21'-1') to prevent pedestrians from colliding with and injured by the handrail sterilizing device 100'. In addition, the light transparent portion 21'-3' is installed in an upper central portion of the front cover 21'. The light transparent portion 21'-3' serves to transmit the light emitted from the indicator light emitting unit therethrough. That is, when the power is generated from the self power source unit 30' and is rectified and stabilized in the power source board 40', and power source is supplied to the ultraviolet lamp modules 50', the indicator light emitting unit 41' also emits the light, and when the light of the indicator light emitting unit 41' is irradiated to the outside through the light transparent portion 21'-3', the pedestrians and a manager recognize that the self-powered type handrail sterilizing device 100' is normally operated, and the handrail sterilizing device 100' has a very attractive form in terms of a design.

In addition, a lower round portion 21'-2 is formed on a lower surface of the front cover 21'. When the self-powered type handrail sterilizing devices 100' according to the present invention are installed at lower sides of the escalator (see FIG. 1), a risk of an accident due to foreign materials such as shoe strings, bag strings, clothes, and the like, inserted between the self-powered type handrail sterilizing devices 100' and the escalator occurs. According to an exemplary embodiment, the lower round portion 21'-2 may be formed to prevent the occurrence of the problem described above.

Meanwhile, the side cover 23' may be configured to include a side cover base 23'-1' in which a circular recess 23'-2 and a fastening hole 23'-3' formed in the center of the circular recess 23'-2 are formed, an O-ring portion 23'-4 fitted into the circular recess 23'-2, and a screw fastening portion 23'-5 screw-coupled to the fastening hole 23'-3' to fasten the side cover base 23'-1' and the frame 10' to each other and having a head portion having the same thickness as a depth of the circular recess 23'-1'. Therefore, the screw fastening portion 23'-5 is rotated to fasten or separate the side cover 23' to or from the frame 10'. In the case in which the side cover 23' needs to be disassembled for the purpose of maintenance, the side cover 23' may be simply separated by rotating the screw fastening portion 23'-5 positioned at the center of the side cover 23'. In addition, the side cover 23' further includes the O-ring portion 23'-4 to be excellent in terms of a design, and the screw fastening portion 23'-5 is configured to be rotatable by frictional force of a finger without using a separate tool.

An upper edge of the side cover 23' may be rounded (a side cover round portion 23'-8) after the side round portion 21'-1' of the front cover 21' to be beautiful in terms of a design and prevent an accident.

Figure 11:
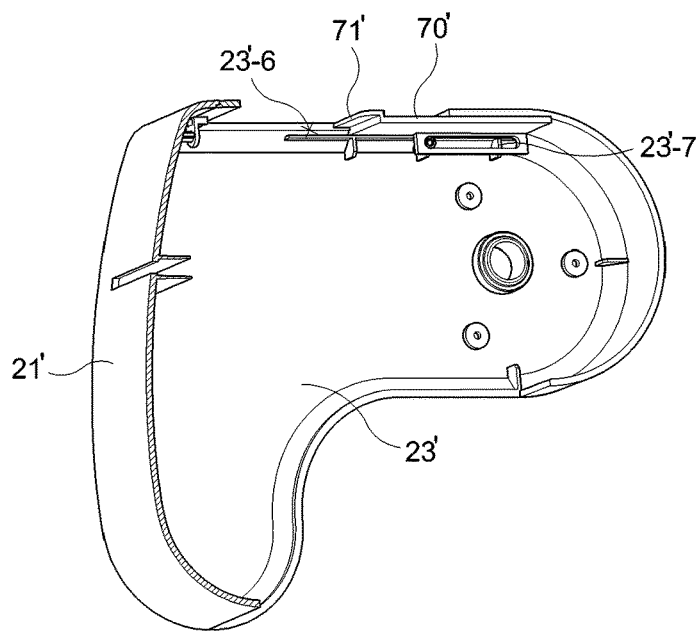
FIG. 11 is a view for describing a sliding door portion of the self-powered type handrail sterilizing device according to a second exemplary embodiment of the present invention.

FIG. 11 is a view for describing a sliding door portion of the self-powered type handrail sterilizing device according to a second exemplary embodiment of the present invention. As illustrated in FIG. 11, the sliding door portion 70' is coupled to a rail 23'-7 installed at an inner side of an opening 23'-6 of the side cover 23'. In addition, the sliding door portion 70' may be configured to include a knob portion 71'. Therefore, a person installing the self-powered type handrail sterilizing device 100' according to the present invention may extend or contract the sliding door portion 70' in a state in which he/she holds the knob portion 71' depending on a width of the handrail. That is, therefore, it is possible to prevent foreign materials such as fine dust, and the like, from entering the self-powered type handrail sterilizing device 100'.

Figure 12:
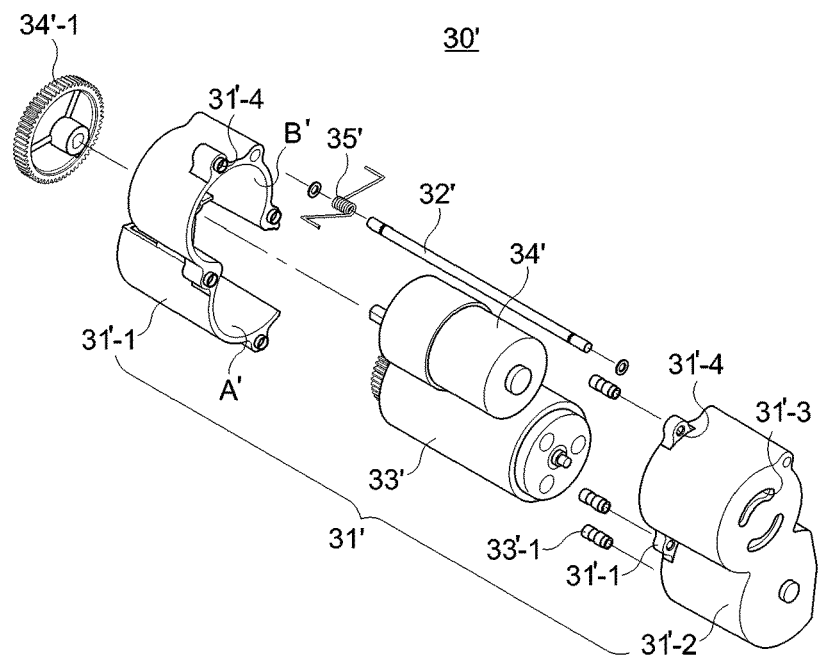
FIG. 12 is an exploded perspective view illustrating a self power source unit of the self-powered type handrail sterilizing device according to a second exemplary embodiment of the present invention.

FIG. 12 is an exploded perspective view illustrating a self power source unit of the self-powered type handrail sterilizing device according to a second exemplary embodiment of the present invention. As illustrated in FIG. 12, the self power source unit 30' used in the self-powered type handrail sterilizing device 100' according to an exemplary embodiment of the present invention may be configured to include a power source case 31' including a first side power source case 31'-1' and a second side power source case 31'-2, a support rod 32', a roller unit 33', a power generating unit 34', and a spring 35'.

The power source case portion 31' includes a first region A' and a second region B' formed by screw-coupling the first side power source case 31'-1' and the second side cover case 31'-2 to each other. The power source case portion 31' may be formed of a thermally conductive plastic material to conduct heat of the power generating unit 34 to the outside and have excellent moldability. In addition, heat radiation holes 31'-3' for radiating the heat of the power generating unit 34 may be formed in side surfaces of the power source case portion 31'.

The support rod 32' is installed to penetrate through fastening holes 31'-4 formed in the power source case portion 31' as illustrated in FIG. 12 to allow the self power source unit 30' to be installed in the frame 10' The spring 35' is fitted onto the support rod 32', and has one end bent to support the power source case 31' and the other end bent to be supported by the frame 10'. Therefore, in a no-load state, the power source case portion 31' is horizontally maintained by the spring 35', and as the self-powered type handrail sterilizing device 100' is mounted at the handrail H, the self-powered type handrail sterilizing device 100' is pressedly rotated by the spring 35, such that the self-powered type handrail sterilizing device 100' is pressedly closely adhered to the handrail H'.

Meanwhile, the roller unit 33' is formed of a material having high frictional force, such as rubber, and has roller gears 33'-1', installed on a side surface thereof, and the roller gears 33'-1' interlock with a power generating gear 34'-1' to transfer a torque of the roller unit 33' generated by the handrail to the power generating unit 34. The power generating unit 34' converts the torque of the roller unit 33' as described above into power, and supplies the power to the power source board 40'.

Figure 13:
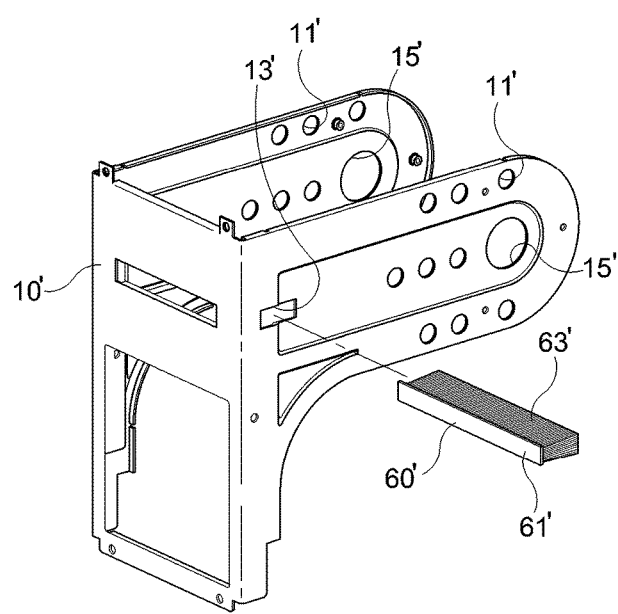
FIG. 13 is a view for describing attachment of a brush hole of the self-powered type handrail sterilizing device according to a second exemplary embodiment of the present invention.

FIG. 13 is a view for describing attachment of a brush hole of the self-powered type handrail sterilizing device according to a second exemplary embodiment of the present invention. As illustrated in FIG. 13, there are a plurality of holes 11', 13', and 15' in side surfaces of the frame 10', and there is a brush groove 13' among the plurality of holes 11', 13', and 15'. The brush groove 13' has a length corresponding to a height of the brush 60', and has a brush rail (not illustrated) extended therefrom. The brush 60' penetrates through the brush groove 13' in a state in which it horizontally lies down, and a fixed portion 61' of the brush 60' is fitted into the brush rail, such that the brush 60' is fixed, as illustrated in FIG. 13. That is, the handrail brush 60' includes the fixed portion 61' fitted into the brush rail and a brush portion 63' attached to an upper surface of the fixed portion, and is detachably and slidably coupled to the frame 10' by the fixed portion, such that the brush 60' may be simply replaced at the time of being replaced.

Figure 14:
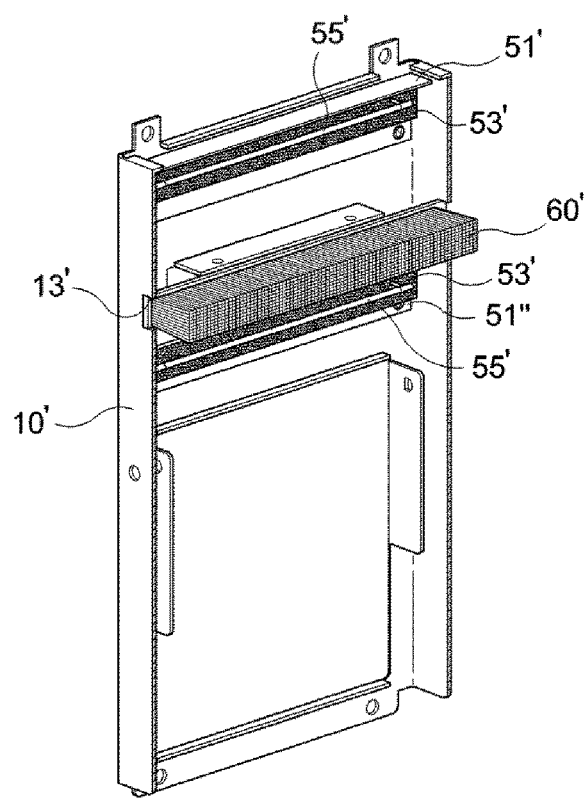
FIG. 14 is a view for describing structures of an ultraviolet lamp and a brush of the self-powered type handrail sterilizing device according to a second exemplary embodiment of the present invention.

FIG. 14 is a view for describing structures of an ultraviolet lamp and a brush 60' of the self-powered type handrail sterilizing device according to a second exemplary embodiment of the present invention. As illustrated in FIG. 14, in the self-powered type handrail sterilizing device 100' according to an exemplary embodiment of the present invention, the pair of ultraviolet lamp modules 50' are attached to the frame, and the handrail brush 60' for removing the fine dust, and the like, attached to the handrail is positioned between the pair of ultraviolet lamp modules 50'.

The ultraviolet lamp modules 50' may include reflecting plates 51 and 51' attached to an inner side of the front of the frame 10' to reflect light generated from ultraviolet lamps toward the handrail, lamp boards 53' installed on the reflecting plates, and the ultraviolet lamps 55' attached to one surfaces of the lamp boards to irradiate the sterilizing light toward the handrail H. The lamp boards 53' and the ultraviolet lamps 55' of the ultraviolet lamp modules 50' may be modularized and be attached to the reflecting plates 51' and 51", and in the case in which a problem occurs in the ultraviolet lamps 55' or the lamp boards 53', modularized components may be simply replaced and used.

Meanwhile, the reflecting plate 51' positioned at an upper side, of the reflecting plates 51' and 51" may have a bent shape such as " ⌐ " so that the light of the ultraviolet lamp 55'; is not exposed to the outside.

Meanwhile, a cathode-ray tube that is cheap may be used as the ultraviolet lamp.

According to an exemplary embodiment of the present invention having the configuration described above, the self-powered type handrail sterilizing device may be mounted at the existing escalator or moving walk in a simple structure, and may sterilize harmful bacteria inhabited in the handrail to contribute to public health.

In addition, according to an exemplary embodiment of the present invention, the cover case is rounded to prevent bags or foreign materials from being fitted into the handrail and the self-powered type handrail sterilizing device according to the present invention at the time of installing the self-powered type handrail sterilizing device at the escalator or the moving walk, thereby making it possible to prevent occurrence of a fault.

Further, according to an exemplary embodiment of the present invention, a simple replacing structure for a cleaning brush is formed, thereby making it possible to improve convenience in maintenance.

In addition, the irradiation range of the sterilizing light is increased, thereby making it possible to maximize the sterilizing effect.

In addition, information on persons visiting through the escalator, or the like, is collected, thereby making it possible to provide basic information on calculation of an advertisement cost for an advertisement, or the like, installed in the vicinity of the escalator.

The handrail sterilizing device and the device for collecting visitor information using the same as described above are not restrictively applied to the configurations and the methods of the exemplary embodiments described above, but all or some of the exemplary embodiments may be selectively combined with each other so that various modifications may be made.

The invention claimed is:

1. A self-powered type handrail sterilizing device comprising:
   a housing having an opening fastened to a handrail of an escalator or a moving walk;
   a power unit installed at an inner side of the housing to convert a rotational motion depending on driving of the handrail into power; and
   a ultraviolet lamp module installed on an inner surface of the opening of the housing and configured to irradiate sterilizing light to the handrail through the power of the power unit,
   wherein the ultraviolet lamp module includes:
      a board attached to an inner peripheral surface of the opening of the housing;
      an ultraviolet lamp attached to one surface of the board to irradiate the sterilizing light toward the handrail; and
      a cleaning brush fixed to an inner peripheral surface of the housing to remove foreign material from the handrail, and
   the ultraviolet lamp includes a first sub-lamp and a second sub-lamp installed with the cleaning brush interposed therebetween.

2. The self-powered type handrail sterilizing device of claim 1, wherein the power unit includes:
   a roller unit movably closely adhered to a main surface of the handrail and rotated;
   a gear unit configured to interlock with the roller unit; and
   a power generating unit configured to generate the power by interlocking with the gear unit.

3. The self-powered type handrail sterilizing device of claim 2, wherein the power unit further includes a pressing unit configured to press the roller unit.

4. The self-powered type handrail sterilizing device of claim 1, wherein the ultraviolet lamp is installed to irradiate the sterilizing light in a direction parallel with a moving direction of the handrail, and the ultraviolet lamp module further includes a lampshade-like reflector configured to reflect the sterilizing light toward the handrail.

5. A self-powered type handrail sterilizing device comprising:
   a frame having a handrail fastening groove formed therein;
   a cover case covering the frame and having an opening, into which the handrail is fitted;
   a self power source unit installed at an inner side of the frame and pressed against the handrail to convert rotational motion of the handrail into a power source;
   a power source board installed at any one of an outer side of the frame and an inner side of the cover case to rectify and stabilize the power source of the self power source unit; and
   a ultraviolet lamp module installed at the inner side of the frame to receive the power source from the power source board and irradiate sterilizing light to the handrail;

wherein the self power source unit includes:
a power source case divided into a first region and a second region;
a support rod for supporting the power source case;
a roller unit installed in the first region and closely adhered to a main surface of the handrail to be thus rotated depending on driving of the handrail;
a power generating unit installed in the second region and configured to generate the power source by interlocking with the roller unit; and
a spring fitted onto the support rod to pressedly closely adhere the power source case to the handrail.

6. The self-powered type handrail sterilizing device of claim 5, wherein the power source case includes:
a first power source side case;
a second power source side case having a mirror shape with respect to the first power source side case; and
a power source fastening portion fastening the first power source side case and the second power source side case to each other.

7. A self-powered type handrail sterilizing device comprising:
a frame having a handrail fastening groove formed therein; a cover case covering the frame and having an opening into which the handrail is fitted;
a self power source unit installed at an inner side of the frame and pressed against the handrail to convert a rotational motion of the handrail into a power source;
a power source board installed at any one of an outer side of the frame and an inner side of the cover case to rectify and, stabilize the power source of the self power source unit; and
a ultraviolet lamp module installed at the inner side of the frame to receive the power source from the power source board and irradiate sterilizing light to the handrail;
wherein the ultraviolet lamp module includes:
a reflecting plate attached to an inner side of a front of the frame;
a board installed on the reflecting plate;
ultraviolet lamps attached to one surface of the board to irradiate the sterilizing light toward the handrail, and installed in pair; and
a handrail brush installed between the ultraviolet lamps, and the handrail brush being detachably attached to the frame, and
wherein a brush rail extended from the brush groove is formed in the frame, and the handrail brush includes a fixed portion fitted into the brush rail, and a brush portion attached to an upper surface of the fixed portion.

8. A self-powered type handrail sterilizing device comprising:
a housing having an opening fastened to a handrail of an escalator or a moving walk;
a power unit installed at an inner side of the housing to convert rotational motion of the handrail into power; and
a ultraviolet lamp module installed on an inner surface of the opening of the housing and configured to irradiate sterilizing light at the handrail via the power of the power unit;
wherein a protecting cover surrounds an outer portion of the housing;
an indicator lamp is installed on the other surface of the board to emit light through the power of the power unit; and
the protecting cover further includes a light transparent portion formed at a position corresponding to that of the indicator lamp.

9. A device for collecting visitor information using a handrail sterilizing device, comprising:
the self-powered type handrail sterilizing devices of claim 1 installed at both sides of a handrail of an escalator to face each other,
wherein at least one of the self-powered type handrail sterilizing devices includes:
a detecting sensor configured to sense a person passing through the escalator;
a communication module configured to transmit and receive data to and from an external device; and
a controller configured to transmit information on a visitor, basic information for calculating an advertisement cost, transmitted from the detecting sensor through the communication module.

10. A self-powered type handrail sterilizing device comprising:
a frame having a handrail fastening groove formed therein;
a cover case covering the frame and having an opening into which the handrail is fitted;
a self power source unit installed at an inner side of the frame and pressedly closely adhered to the handrail to convert a rotational motion depending on driving of the handrail into power source;
a power source board installed at any one of an outer side of the frame and an inner side of the cover case to rectify and stabilize the power source of the self power source unit; and
a ultraviolet lamp module installed at the inner side of the frame to receive the power source from the power source board and irradiate sterilizing light to the handrail,
wherein the cover case includes:
a front cover corresponding to a front of the frame and having both side surfaces rounded in order to protect a pedestrian; and
a pair of side covers installed at both sides of the front cover;
the side cover includes:
a side cover base in which a circular recess and a fastening hole formed in the center of the circular recess are formed; and
a screw fastening portion screw-coupled to the fastening hole to fasten the side cover base and the frame to each other and having a head portion having a size corresponding to a size of the circular recess.

11. The self-powered type handrail sterilizing device of claim 10, wherein a lower surface of the front cover is rounded in order to prevent an external object from being inserted into the handrail.

12. The self-powered type handrail sterilizing device of claim 10, further comprising a sliding door portion installed in an opening of each of the side covers to adjust a size of the opening depending on a size of the handrail.

13. The self-powered type handrail sterilizing device of claim 10, wherein a heat radiation hole is formed in the power source case in order to radiate heat of the power generating unit.

* * * * *